United States Patent [19]

Wade et al.

[11] 4,177,191
[45] Dec. 4, 1979

[54] 2-ALKYL-3-(SUBSTITUTED HYDRAZINO)BENZISOTHIAZOLINES

[75] Inventors: Peter C. Wade, Pennington, N.J.; B. Richard Vogt, Yardley, Pa.; Thomas P. Kissick, Princeton, N.J.

[73] Assignee: E. R. Squibb & Sons, Inc., Princeton, N.J.

[21] Appl. No.: 926,467

[22] Filed: Jul. 20, 1978

[51] Int. Cl.$^2$ ............... A61K 31/425; C07D 275/04
[52] U.S. Cl. .......................... 548/212; 424/270; 424/232
[58] Field of Search ...................... 260/304 A

[56] References Cited
PUBLICATIONS

Böshagen, H. et al., Chem. Ber. 103, (1970), pp. 3166–3181.
Hünig, S. et al., Liebigs Ann. Chem. 748, (1971), pp. 201–206.
Böshagen, H. et al., Chem. Ber. 109, (1976), pp. 659–668.

*Primary Examiner*—Alton D. Rollins
*Assistant Examiner*—Lisa Jones
*Attorney, Agent, or Firm*—Lawrence S. Levinson; Donald J. Barrack

[57] ABSTRACT

Benzisothiazolines having the formula

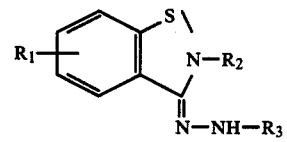

wherein
 $R_1$ is hydrogen, alkyl, alkoxy, halogen or nitro;
 $R_2$ is alkyl; and $R_3$ is (i)

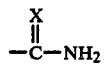

wherein X is oxygen, sulfur or imino or (ii)

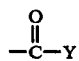

wherein Y is alkoxy, alkyl, or arylalkyl, have useful pharmacological activity.

15 Claims, No Drawings

2-ALKYL-3-(SUBSTITUTED HYDRAZINO)BENZISOTHIAZOLINES

BRIEF DESCRIPTION OF THE INVENTION

Compounds having the formula

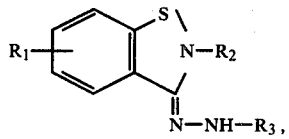

I and the pharmaceutically acceptable salts thereof, have useful pharmacological activity. In formula I, and throughout the specification, the symbols are as defined below.

$R_1$ is hydrogen, alkyl, alkoxy, halogen or nitro;
$R_2$ is alkyl; and
$R_3$ is (i)

wherein X is oxygen, sulfur or imino, or (ii)

wherein Y is alkoxy, alkyl or arylalkyl.

The terms "alkyl" and "alkoxy," as used throughout the specification (whether alone or as part of a larger group), refer to groups having 1 to 6 carbon atoms; groups having 1 to 3 carbon atoms are preferred.

The term "halogen," as used throughout the specification (whether alone or as part of a larger group), refers to fluorine, chlorine, bromine and iodine, bromine and chlorine are preferred.

The term "aryl," as used throughout the specification (whether alone or as part of a larger group), refers to phenyl or phenyl substituted with a halogen, alkyl, alkoxy, hydroxy or nitro group.

DETAILED DESCRIPTION OF THE INVENTION

The compounds of formula I can be prepared by reacting a 2-alkyl-3-halo-1,2-benzisothiazolium salt (preferably a 2-alkyl-3-chloro-1,2-benzisothiazolium halide) having the formula

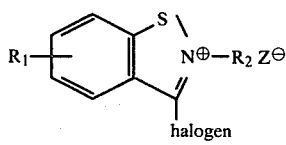

II with a compound having the formula

III

In the above formula, and throughout the specification, the symbol "Z" represents a pharmaceutically acceptable anion. The reaction can be run in an organic solvent, preferably a lower alkanol such as ethanol, in the optional presence of an organic base such as triethylamine.

The above reaction yields a pharmaceutically acceptable salt of the product of formula I. This salt will exist as a tautomeric mixture which can be represented by the following formulas:

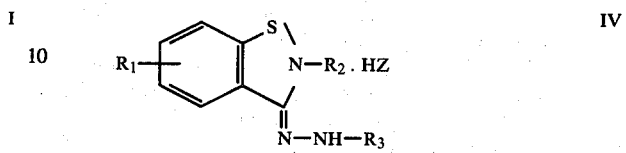

IV

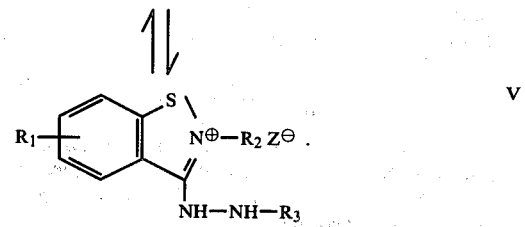

V

The starting materials of formula II are known in the art; see, for example, Chem. Ber., 99,2566-2571 (1966). The starting compounds of formula III are also known in the art; some are commercially available, and all are readily obtainable via conventional synthetic routes.

The tautomeric mixture made up of the salts of formulas IV and V can be converted into the corresponding free base of formula I using art-recognized procedures. The free bases of formula I can then be converted into other pharmaceutically acceptable salts. The acid-addition salts are specifically contemplated; e.g., the hydrohalides (the hydrochloride and hydrobromide are preferred), sulfate, nitrate, phosphate, borate, acetate, tartrate, maleate, citrate, succinate, benzoate, ascorbate, salicylate, methanesulfonate, benzenesulfonate, toluenesulfonate, and the like.

The compounds of formula I, and the pharmaceutically acceptable salts thereof, can be used to treat various allergic conditions in mammals when administered in amounts ranging from about 1 milligram to about 500 milligrams per kilogram of body weight per day. The products of this invention can be used prophylactically or therapeutically to treat various allergic and immunological disorders and in particular to treat certain types of asthma, hay-fever and rhinitis. They are anti-allergics which inhibit the effects of certain antigen-antibody reactions and, in particular, inhibit the release of mediators such as histamine. The anti-allergy activity of these compounds can be determined by the reaginic antibody induced passive cutaneous anaphylaxis reaction in rats (see Bach, Immediate Hypersensitivity: Laboratory Models and Experimental Findings, Ann. Rep. Med. Chem., 7:238-248 (1972) for a discussion of the predictability of clinical efficacy of compounds active in this test.

The compounds of formula I, and the pharmaceutically acceptable salts thereof, can also be used to treat inflammation in mammals. Joint tenderness and stiffness (in conditions such as rheumatoid arthritis) can be reduced by these compounds. The compounds of this invention can be administered in amounts of 100 milligrams to 2 grams per kilogram of animal body weight per day, preferably 100 milligrams to 1 gram per kilogram of animal body weight per day.

The following examples are specific embodiments of this invention.

EXAMPLE 1

3-[2-Aminocarbonyl)hydrazino]-2-ethyl-1,2-benzisothiazolium chloride

Semicarbazide hydrochloride (21.45 g) is dissolved in a mixture of 300 ml of ethanol and 26.8 ml of triethylamine by brief warming. To the warm solution is added 15.0 g of 3-chloro-2-ethyl-1,2-benzisothiazolium chloride and the mixture is stirred for about 16 hours. The product (plus some unreacted semicarbazide hydrochloride) crystallizes out and is filtered off, washed with ethanol, and recrystallized from 450 ml methanol/40 ml water to yield 10.8 g of the title compound, effervesence at 224° C.

EXAMPLES 2-6

Following the procedure of Example 1, but substituting the compound listed in column I for semicarbazide hydrochloride and the compound listed in column II for 3-chloro-1,2-benzisothiazolium chloride, yields the compounds listed in column III.

|    | Column I | Column II | Column III |
| --- | --- | --- | --- |
| 2. | thiosemicarbazide | 3,6-diochloro-2-ethyl-1,2-benzisothiazolium chloride | 3-[2-[amino(thiocarbonyl)]-hydrazino]-2-ethyl-1,2-benzisothiazolium chloride |
| 3. | aminoguanidine bicarbonate | 3-chloro-2,6-diethyl-1,2-benzisothiazolium chloride | 3-[2-(aminoiminoethyl) hydrazino]-2,6-diethyl-1,2-benzisothiazolium chloride |
| 4. | methyl hydrazinocarboxylate | 3-chloro-6-methoxy-2-methyl-1-1,2-benzisothiazolium chloride | 6-methoxy-2-methyl-3-[2-(methoxycarbonyl)-hydrazino]1,2-benzisothiazolium chloride |
| 5. | acetylhydrazine | 3-chloro-6-nitro-2-(n-propyl)-1,2-benzisothiazolium chloride | 3-(2-acetylhydrazino)-6-nitro-2-(n-propyl)-1,2-benzisothiazolium chloride |
| 6. | (4-flourophenyl)-acetylhydrazine | 3-chloro-2-methyl-1,2-benzisothiazolium chloride | 3-[2-[(4-flourophenyl) acetyl]hydrazino]-2-methyl-1,2-benzisothiazolium chloride |

What is claimed is:

1. A compound having the formula

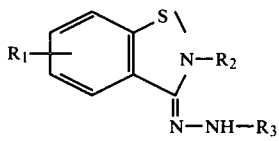

or a pharmaceutically acceptable salt thereof, wherein $R_1$ is hydrogen, alkyl, alkoxy, halogen or nitro; $R_2$ is alkyl; and $R_3$ is (i)

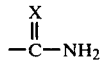

wherein X is oxygen, sulfur or imino, or (ii)

wherein Y is alkoxy, alkyl, or arylalkyl; wherein the terms "alkyl" and "alkoxy" refer to groups having 1 to 6 carbon atoms and the term "aryl" refers to phenyl or phenyl substituted with a halogen, alkyl, alkoxy, hydroxy or nitro group.

2. A compound in accordance with claim 1 wherein $R_1$ is hydrogen.

3. A compound in accordance with claim 1 wherein $R_1$ is alkyl.

4. A compound in accordance with claim 1 wherein $R_1$ is alkoxy.

5. A compound in accordance with claim 1 wherein $R_1$ is halogen.

6. A compound in accordance with claim 1 wherein $R_1$ is nitro.

7. A compound in accordance with claim 1 wherein $R_3$ is

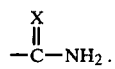

8. A compound in accordance with claim 7 wherein X is oxygen.

9. A compound in accordance with claim 7 wherein X is sulfur.

10. A compound in accordance with claim 7 wherein X is imino.

11. A compound in accordance with claim 1 wherein $R_3$ is

12. A compound in accordance with claim 11 wherein Y is alkoxy.

13. A compound in accordance with claim 11 wherein Y is alkyl.

14. A compound in accordance with claim 11 wherein Y is arylalkyl.

15. The compound in accordance with claim 1 having the name 3-[2-(aminocarbonyl)hydrazino]-2-ethyl-1,2-benzisothiazolium chloride.

* * * * *